(12) United States Patent
Pillai et al.

(10) Patent No.: US 11,103,057 B2
(45) Date of Patent: Aug. 31, 2021

(54) ORAL CARE IMPLEMENT

(71) Applicant: Colgate-Palmolive Company, New York, NY (US)

(72) Inventors: Shyamala Pillai, Hillsborough, NJ (US); Remo Villiger, Sempach (CH); Marco Bohner, Sempach (CH); Peter Zurfluh, Alpnach-Dorf (CH)

(73) Assignee: Colgate-Palmolive Company, New York, NY (US)

( * ) Notice: Subject to any disclaimer, the term of this patent is extended or adjusted under 35 U.S.C. 154(b) by 25 days.

(21) Appl. No.: 16/200,745

(22) Filed: Nov. 27, 2018

(65) Prior Publication Data

US 2019/0159582 A1   May 30, 2019

Related U.S. Application Data

(60) Provisional application No. 62/590,827, filed on Nov. 27, 2017.

(51) Int. Cl.
*A46B 11/00* (2006.01)
*A45D 40/00* (2006.01)
(Continued)

(52) U.S. Cl.
CPC .......... *A46B 11/0068* (2013.01); *A45D 40/00* (2013.01); *A46B 9/025* (2013.01); *A46B 9/04* (2013.01); *A46B 11/001* (2013.01); *A46B 11/0072* (2013.01); *A46B 15/0085* (2013.01); *A61K 8/19* (2013.01); *A61K 8/27* (2013.01); *A61K 8/44* (2013.01); *A61K 8/8176* (2013.01); *A61K 8/88* (2013.01); *A61Q 11/00* (2013.01); *A46B 2200/1066* (2013.01); *B29C 45/0001* (2013.01); *B29K 2995/0062* (2013.01)

(58) Field of Classification Search
CPC ... A46B 11/00; A46B 11/0003; A46B 11/001; A46B 2200/1066
See application file for complete search history.

(56) References Cited

U.S. PATENT DOCUMENTS 5,340,581 A   8/1994   Tseng et al.
5,723,132 A   3/1998   Tseng et al.
(Continued)

FOREIGN PATENT DOCUMENTS

WO   2007/025012   3/2007
WO   2009/136911   11/2009

OTHER PUBLICATIONS

BASF, 2010, "Pharma Ingredients & Services = Registered trademark of BASF group Soluplus Technical Information Supersedes" p. 1-8 https://industries.basf.com/en/documentDownload.8805242743253.Soluplus%20-%20Technical%20Information.pdf (retrieved on Feb. 13, 2019).

(Continued)

*Primary Examiner* — David P Angwin
*Assistant Examiner* — Bradley S Oliver

(57) ABSTRACT

Described herein is an oral care implement comprising a handle, and a head having a main body that is coupled to the handle, the head comprising a release component coupled to the main body, the release component comprising a water-dissolvable matrix comprising a first polymer having a processing temperature greater than or equal to 150° C., and a plurality of tooth cleaning elements.

20 Claims, 6 Drawing Sheets

(51) Int. Cl.

| | |
|---|---|
| *A46B 9/02* | (2006.01) |
| *A46B 9/04* | (2006.01) |
| *A46B 15/00* | (2006.01) |
| *A61K 8/19* | (2006.01) |
| *A61K 8/27* | (2006.01) |
| *A61K 8/44* | (2006.01) |
| *A61K 8/81* | (2006.01) |
| *A61K 8/88* | (2006.01) |
| *A61Q 11/00* | (2006.01) |
| *B29C 45/00* | (2006.01) |

(56) References Cited

U.S. PATENT DOCUMENTS

| | | |
|---|---|---|
| 5,906,834 A | 5/1999 | Tseng |
| 6,108,847 A | 8/2000 | Cueman et al. |
| 6,119,296 A | 9/2000 | Noe et al. |
| 7,357,949 B2 | 4/2008 | Trogolo et al. |
| 8,075,216 B2 * | 12/2011 | Gatzemeyer ......... A46B 11/001 401/288 |
| 8,092,110 B2 | 1/2012 | Canady |
| 8,109,686 B2 | 2/2012 | Bartschi et al. |
| 8,322,939 B2 | 12/2012 | Hohlbein et al. |
| 8,376,643 B2 | 2/2013 | Canady |
| 8,632,269 B2 | 1/2014 | Sorrell |

OTHER PUBLICATIONS

Desai et al., 2011, "Fatty acid and water-soluble polymer-based controlled release drug delivery system" PubMed NCBI https://www.ncbi.nlm.nih.gov/pubmed/21374622 [retrieved on Feb. 13, 2019].

International Search Report and the Written Opinion of the International Searching Authority issued in international application PCT/US2018/062503 dated Feb. 20, 2019.

* cited by examiner

ORAL CARE IMPLEMENT

CROSS-REFERENCE TO RELATED APPLICATIONS

This application claims the benefit of U.S. Provisional Application No. 62/590,827, filed on Nov. 27, 2017. The disclosure of the above application is incorporated herein by reference.

BACKGROUND

Toothbrushes comprising water-soluble release polymers are known to provide a release of a desired component to the user. The effect of such water-soluble release polymers was to provide a perceivable response by the user—such as color change—after the water-soluble polymer was exposed to water during usage. However, previously, such water-soluble release polymers have rapid release profiles—releasing the desired component within days of the first usage, thereby making those polymers unsuitable to last the entire lifespan of the oral care implement. Alternatively, such water-soluble release polymers may require low processing temperatures (less than 130° C.) because such polymers undergo severe degradation at temperatures above 130° C., thereby destroying the controlled release characteristics. Having such low processing temperatures creates long manufacturing times.

Thus, there exists a need for an oral care implement comprising a water-soluble release composition that can be formed at high temperatures without undermining the desired release characteristics.

BRIEF SUMMARY

The present invention is directed to an oral care implement comprising a handle; and a head having a main body that is coupled to the handle, the head comprising: a release component coupled to the main body, the release component comprising a water-dissolvable matrix comprising a first polymer having a processing temperature greater than or equal to 150° C.; and a plurality of tooth cleaning elements.

According to other embodiments, the present invention includes an oral care implement comprising a handle; and a head having a main body coupled to the handle, the head comprising a release component comprising a water-dissolvable matrix comprising a graft polymer having units formed from caprolactam, vinyl acetate, and ethylene glycol; and a plurality of tooth cleaning elements.

Other embodiments of the present invention include a method of forming an oral care implement comprising injection molding a composition comprising a graft polymer onto a head of an oral care implement at a temperature equal to or greater than about 150° C. to form a water-dissolvable polymer matrix.

Other embodiments of the present invention include a method of forming an oral care implement comprising injection molding a composition comprising a graft polymer onto a head of an oral care implement at a temperature equal to or greater than about 150° C. to form a water-dissolvable polymer matrix.

In other embodiments, the present invention is directed to a method of forming an oral care implement comprising injection molding a composition comprising a blend of a graft polymer and an additive onto a head of an oral care implement at a temperature equal to or greater than 130° C. to form a water-dissolvable polymer matrix; wherein the additive has a decomposition temperature less than or equal to 150° C.

In other embodiments, the present invention includes a method of forming an oral care implement comprising injection molding a composition comprising a blend of a graft polymer and an additive onto a head of an oral care implement at a temperature equal to or greater than 110° C. to form a water-dissolvable polymer matrix, wherein the additive has a vapor pressure of at least about 0.18 atm at 100° C.

In other embodiments, the present invention is directed to an oral care implement comprising: a handle; and a head having a main body that is coupled to the handle, the head comprising: a front surface and a rear surface, a plurality of open cavities are formed into the rear surface of the head, a release component coupled to the main body positioned in at least one of the plurality of open-ended cavities; and a plurality of tooth cleaning elements; wherein the release component comprises a water-dissolvable matrix comprising a first polymer having a processing temperature greater than or equal to 130° C.

Other embodiments of the present invention include a method of forming an oral care implement comprising: injection molding a composition at a temperature equal to or greater than 130° C. to form a water dissolvable body, the composition comprising a water-dissolvable graft polymer that forms a matrix in the water dissolvable body; positioning the water dissolvable body on a head of an oral care implement.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
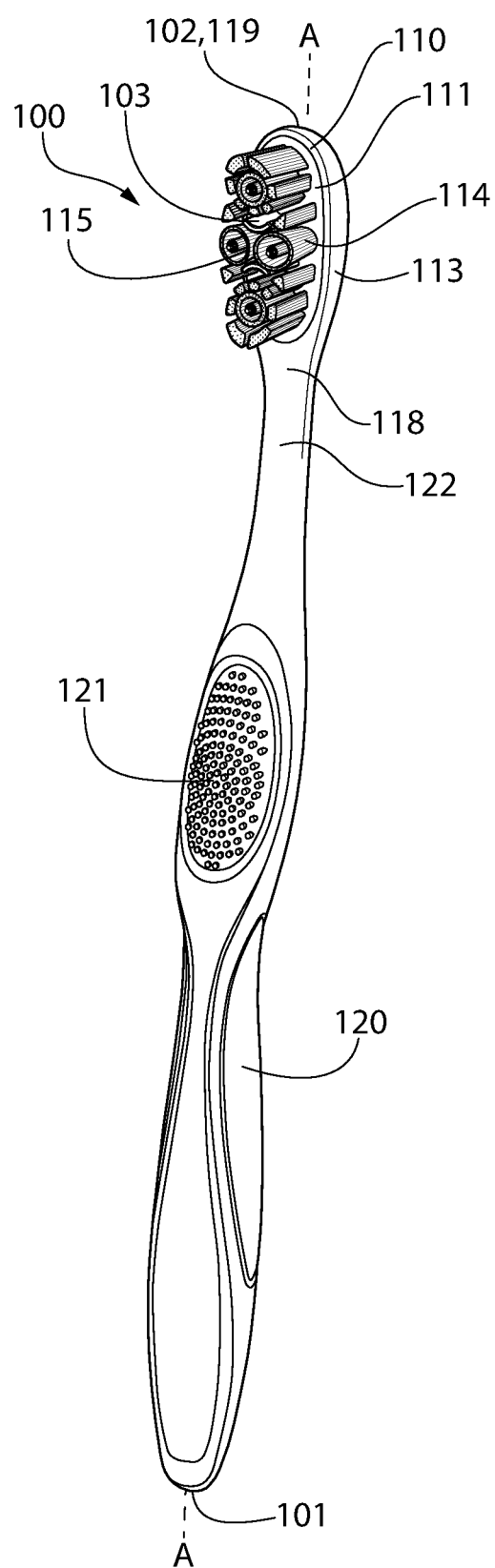
FIG. 1 is front perspective view of an oral care implement in accordance with an embodiment of the present invention.

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top," and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such.

Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Unless otherwise specified, all percentages and amounts expressed herein and elsewhere in the specification should be understood to refer to percentages by weight. The amounts given are based on the active weight of the material. According to the present application, the term "about" means +/−5% of the reference value. According to the present application, the term "substantially free" less than about 0.1 wt. % based on the total of the referenced value.

Figure 2:
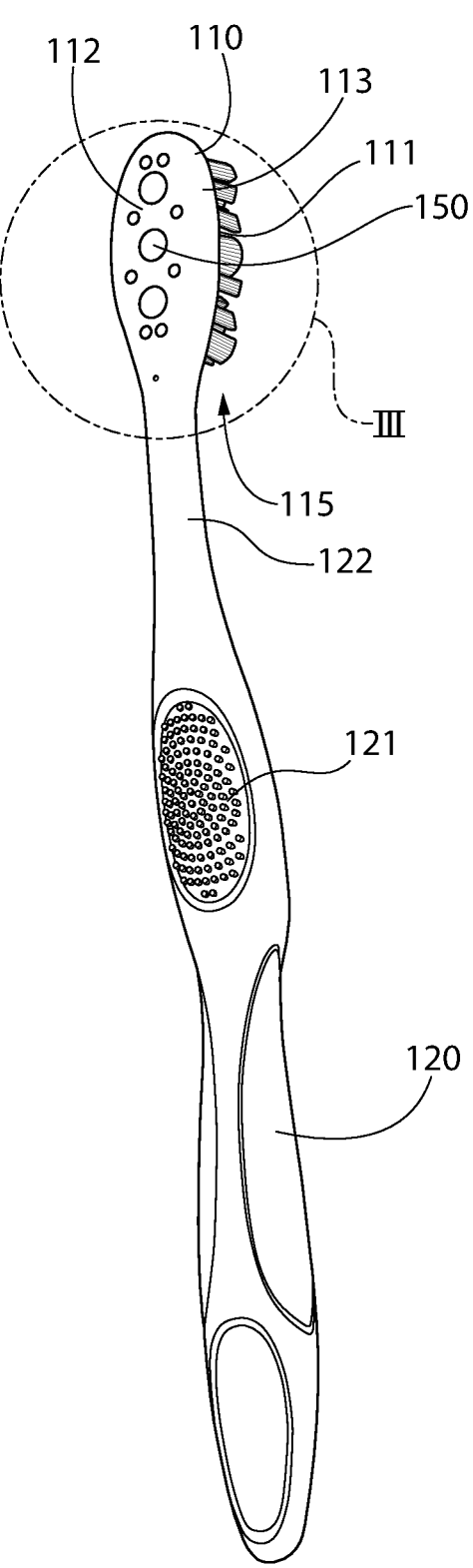
FIG. 2 is a rear perspective view of the oral care implement of FIG. 1.
Figure 3:
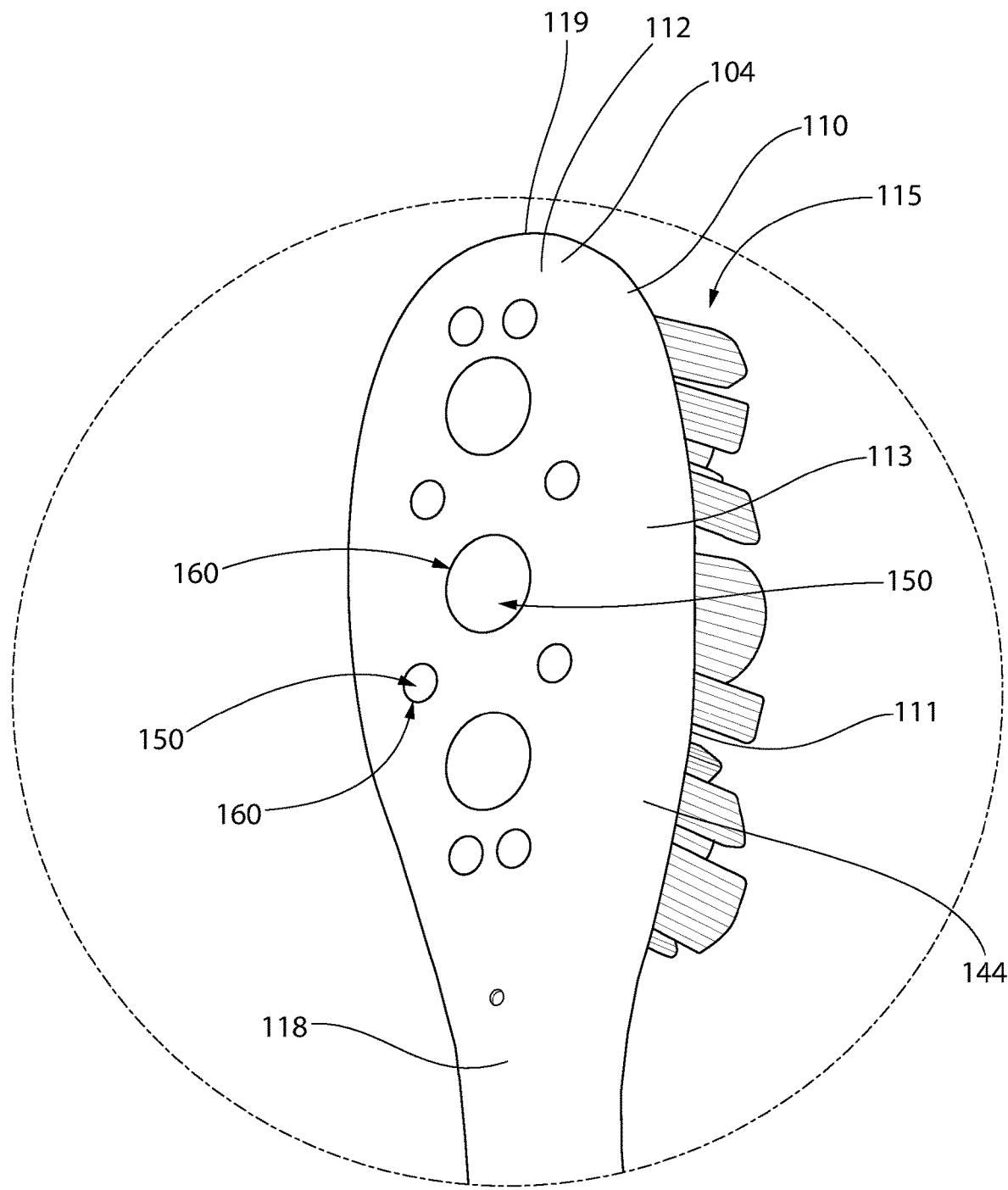
FIG. 3 is a close-up view of area III of FIG. 2.

Referring first to FIGS. 1 and 2 concurrently, an oral care implement 100 is illustrated in accordance with one embodiment of the present invention. In the exemplified embodiment, the oral care implement 100 is in the form of a manual toothbrush. However, in certain other embodiments the oral care implement 100 can take on other forms such as being a powered toothbrush, a tongue scraper, a gum and soft tissue cleanser, a water pick, an interdental device, a tooth polisher, a specially designed ansate implement having tooth engaging elements, or any other type of implement that is commonly used for oral care. Thus, it is to be understood that the inventive concepts discussed herein can be applied to any type of oral care implement unless a specific type of oral care implement is specified in the claims.

The oral care implement 100, which generally comprises a head 110 and a handle 120, extends from a proximal end 101 to a distal end 102 along a longitudinal axis A-A. The head 110 extends from a proximal end 118 to a distal end 119 along a longitudinal axis that is coextensive with the longitudinal axis A-A of the oral care implement 100. Furthermore, in the exemplified embodiment the distal end 102 of the oral care implement 100 is the same as the distal end 119 of the head 110.

The handle 120 is an elongated structure that provides the mechanism by which the user can hold and manipulate the oral care implement 100 during use. In the exemplified embodiment, the handle 120 is generically depicted having various contours for user comfort. Of course, the invention is not to be limited by the specific shape illustrated for the handle 120 in all embodiments and in certain other embodiments the handle 120 can take on a wide variety of shapes, contours, and configurations, none of which are limiting of the present invention unless so specified in the claims. The handle 120 may include a neck portion 122 that extends to the proximal end 118 of the head 110.

In the exemplified embodiment, the handle 120 is formed of a hard or rigid plastic material, such as for example without limitation polymers and copolymers of ethylene, propylene, butadiene, vinyl compounds, and polyesters such as polyethylene terephthalate. The handle 120 also includes a grip 121 that is formed of a resilient/elastomeric material. In the exemplified embodiment, the grip 121 is molded over a portion of the handle 120 that is typically gripped by a user's thumb and forefinger during use. Furthermore, it should be appreciated that additional regions of the handle 120 can be overmolded with the resilient/elastomeric material to enhance the gripability of the handle 120 during use. For example, portions of the handle 120 that are typically gripped by a user's palm during use may be overmolded with a thermoplastic elastomer or other resilient material to further increase comfort to a user. Furthermore, materials other than those noted above can be used to form the handle 120, including metal, wood, or any other desired material that has sufficient structural rigidity to permit a user to grip the handle 120 and manipulate the oral care implement 100 during tooth brushing.

The head 110 of the oral care implement 100 is coupled to the handle 120 and comprises a front surface 111 and an opposing rear surface 112. Furthermore, the head 110 comprises a peripheral surface 113 extending between the rear surface 112 and the front surface 111. In the exemplified embodiment, the head 110 is formed integrally with the handle 120 as a single unitary structure using a molding, milling, machining, or other suitable process. However, in other embodiments the handle 120 and the head 110 may be formed as separate components which are operably connected at a later stage of the manufacturing process by any suitable technique known in the art, including without limitation thermal or ultrasonic welding, a tight-fit assembly, a coupling sleeve, threaded engagement, adhesion, or fasteners. Thus, the head 110 may, in certain embodiments, be formed of any of the rigid plastic materials described above as being used for forming the handle 120, although the invention is not to be so limited in all embodiments and other materials that are commonly used during toothbrush head manufacture may also be used.

As discussed further herein, the oral care implement 100 also comprises a release component 150 extending from the rear surface 112 of the head 110. The oral care implement 100 also comprises a plurality of tooth cleaning elements 115 extending from the front surface 111 of the head 110. The invention is not to be limited by the structure, pattern, orientation, and material of the tooth cleaning elements 115 in all embodiments. Furthermore, where it does not conflict with the other disclosure provided herein or the claims, it should be appreciated that the term "tooth cleaning elements" may be used in a generic sense to refer to any structure that can be used to clean, polish, or wipe the teeth and/or soft oral tissue (e.g. tongue, cheek, gums, etc.) through relative surface contact. Common examples of "tooth cleaning elements" include, without limitation, bristle tufts, filament bristles, fiber bristles, nylon bristles, polybutylene terephthalate (PBT) bristles, spiral bristles, rubber bristles, elastomeric protrusions, flexible polymer protrusions, combinations thereof, and/or structures containing such materials or combinations. Thus, any combination of these tooth cleaning elements may be used within the tooth cleaning elements 115 in some embodiments. Furthermore, where bristles are used for one or more of the tooth cleaning elements 115, such bristles can be tapered, end-rounded, spiral, or the like.

In embodiments that use elastomeric materials to form one or more of the tooth cleaning elements 115, suitable elastomeric materials may include any biocompatible resilient material suitable for uses in an oral hygiene apparatus. To provide optimum comfort as well as cleaning benefits, the elastomeric material of any such tooth cleaning element may have a hardness property in the range of A10 to A70 Shore hardness in one embodiment, or A8 to A25 Shore hardness in another embodiment. One suitable elastomeric material is styrene-ethylene/butylene-styrene block copolymer (SEBS) manufactured by GLS Corporation. Nevertheless, SEBS material from other manufacturers or other materials within and outside the noted hardness range could be used.

Figure 4:
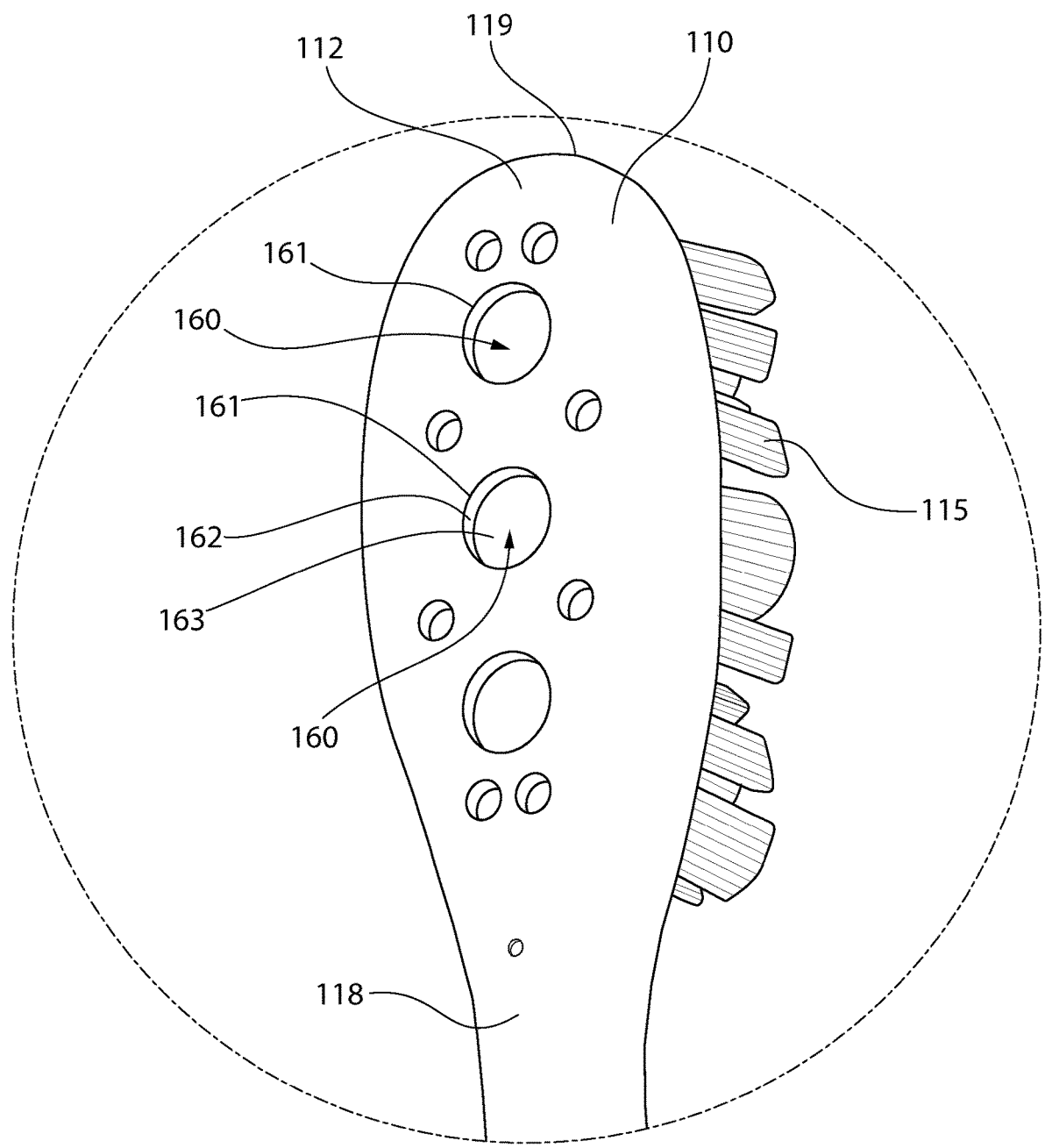
FIG. 4 is a close-up view of area III of FIG. 2 before injection molding a release composition.
Figure 5:
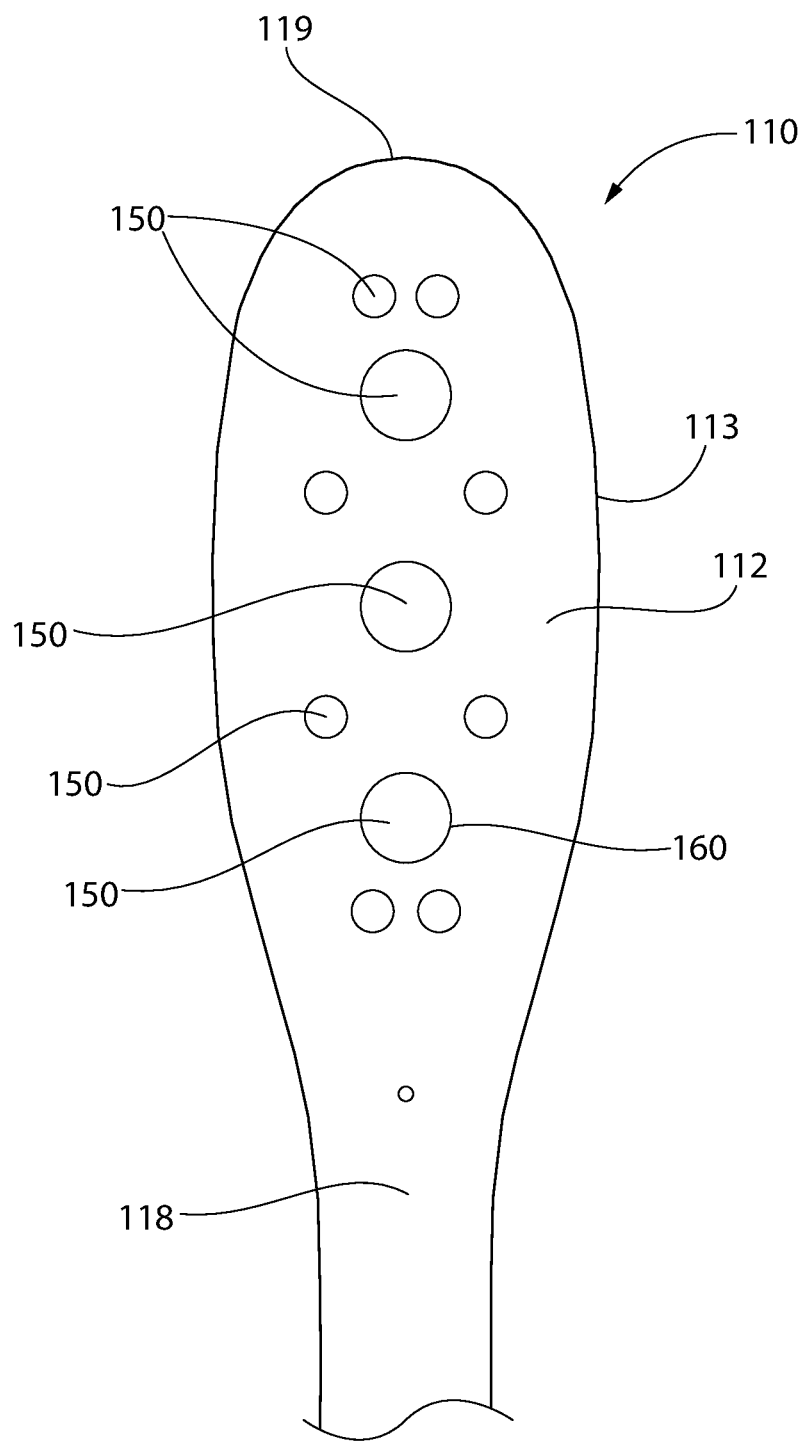
FIG. 5 is a rear view of the head of the oral care implement of FIG. 1.
Figure 6:
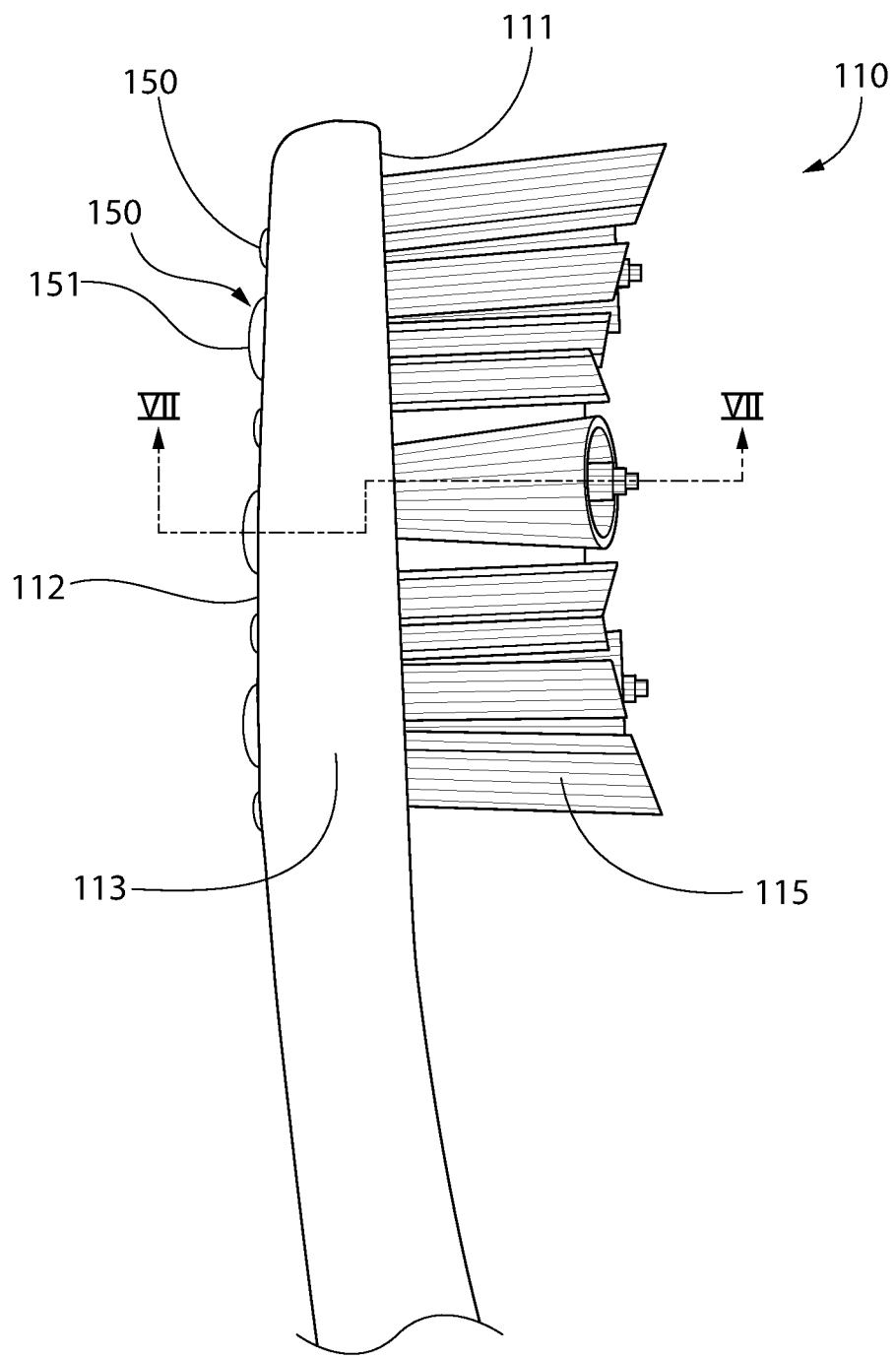
FIG. 6 is a side view of the head of the oral care implement of FIG. 1.
Figure 7:
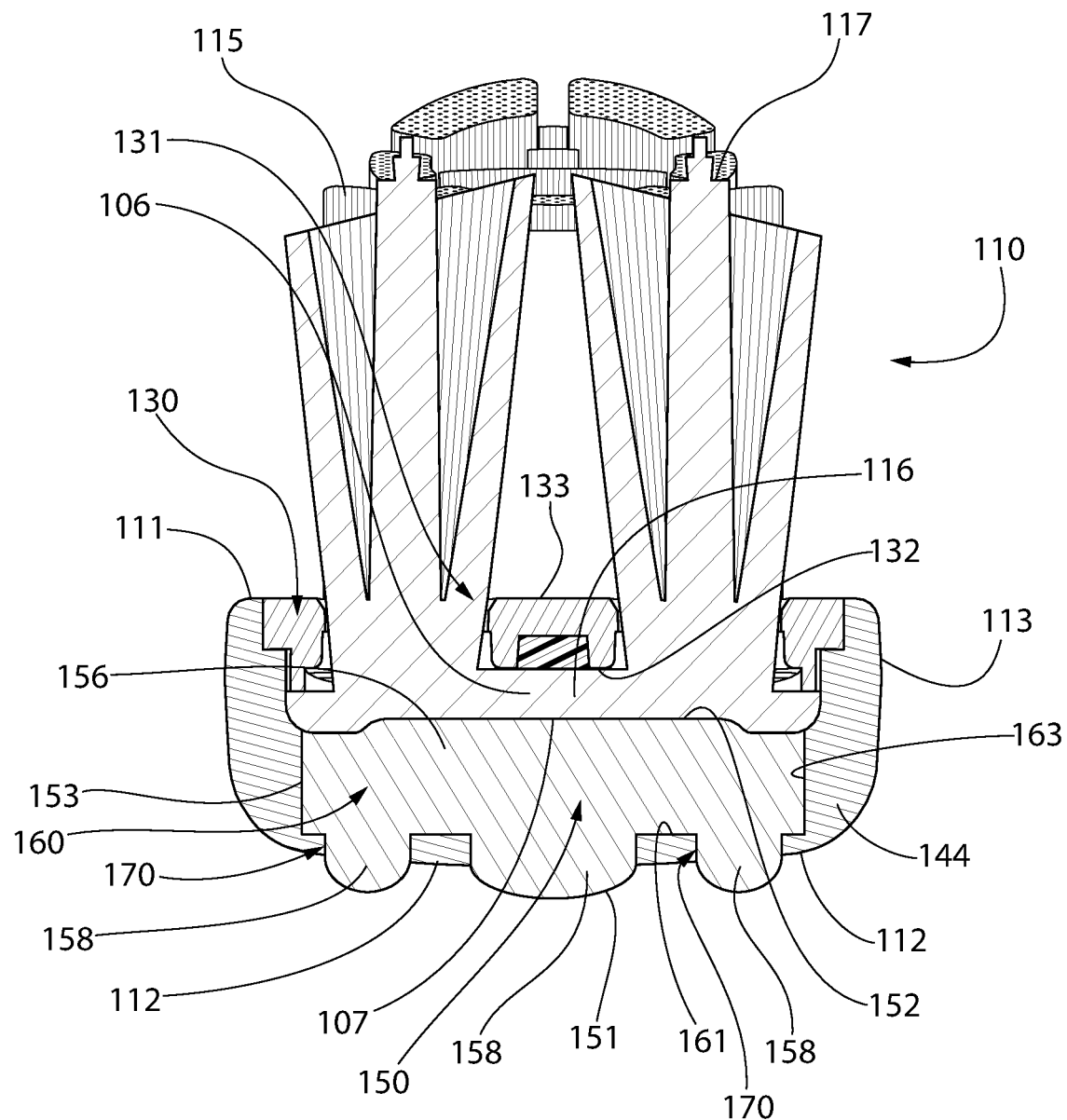
FIG. 7 is a cross-sectional view taken along line VII-VII of FIG. 6.

The tooth cleaning elements 115 may be coupled to the head 110 in any manner known in the art, including staples, in-mold tufting (IMT), anchor-free tufting (AFT), or a modified AFT known as AMR. Referring briefly to FIGS. 4 and 7, one manner in which the tooth cleaning elements 115 are secured to the head 110 via AFT will be described. Specifically, in the embodiment exemplified the tooth cleaning elements 115 are formed as a cleaning element assembly on a head plate 130 such that one or more of the tooth cleaning elements 115 are mounted onto the head plate 130 and then the head plate 130 is coupled to the head 110. In such an embodiment, the head plate 130 is a separate and distinct component from the head 110 of the oral care implement 100. However, the head plate 130 is connected to the head 110 at a later stage of the manufacturing process by any suitable technique known in the art, including without limitation thermal or ultrasonic welding, any fusion techniques such as thermal fusion, melting, a tight-fit assembly, a coupling sleeve, threaded engagement, adhesion, or fasteners. Thus, the head plate 130 and the head 110 are separately formed components that are secured together during manufacture of the oral care implement 100.

In certain embodiments, the head plate 130 may comprise an upper surface 133 and a lower surface 132. The upper surface 133 of the head plate 130 forms a portion of the front surface 111 of the head 110 when the head plate 130 is coupled to the head 110 as discussed herein. The head plate 130 comprises a plurality of holes 131 formed therethrough from the upper surface 133 to the lower surface 132, and the tooth cleaning elements 115 may be mounted to the head plate 130 within the holes 131. Specifically, in AFT a plate or membrane (i.e., the head plate 130) is created separately from the head 110. The tooth cleaning elements 115 (such as bristles, elastomeric elements, and combinations thereof) are positioned into the head plate 130 so as to extend through the holes 131 of the head plate 130. The free ends 117 of the tooth cleaning elements 115 on one side of the head plate 130 perform the cleaning function. The anchor portions 116 of the tooth cleaning elements 115 on the other side of the head plate 130 are melted together by heat to be anchored in place. As the tooth cleaning elements 115 are melted together, a melt matte 106 is formed. The melt matte 106 is a thin layer of plastic that is formed by melting the anchor portions 116 of the bristles so that the anchor portions 116 of the bristles transition into a liquid, at which point the liquid of the anchor portions 116 of the bristles combine together into a single layer of liquid plastic that at least partially covers the lower surface 132 of the head plate 130. After the heat is no longer applied, the melted anchor portions 116 of the bristles solidify/harden to form the melt matte 106 or thin layer of plastic. The melt mattes comprises a lower surface 107 that is opposite the lower surface 132 of the head plate 130.

After the tooth cleaning elements 115 are secured to the head plate 130, the head plate 130 is secured to the head 110 such as by ultrasonic welding or mechanical techniques (i.e., snap-fit, interference fit, slot-and-tab, or the like) so that the upper surface 133 of the head plate 130 forms at least a portion of the front surface 111 of the head 110. When the head plate 130 is coupled to the head 110, the melt matte 106 is located between the lower surface 132 of the head plate 130 and the release component 150—as discussed further herein. The melt matte 106, which is coupled directly to and in fact forms a part of the tooth cleaning elements 115, prevents the tooth cleaning elements 115 from being pulled through the holes 131 in the head plate 130 to ensure that the tooth cleaning elements 115 remain attached to the head plate 130 during use of the oral care implement 100.

As noted above, in another embodiment the tooth cleaning elements may be connected to the head 110 using a technique known in the art as AMR. In this technique, the handle is formed integrally with the head plate as a one-piece structure. After the handle and the head plate are formed, the bristles are inserted into holes in the head plate so that the free/cleaning ends of the bristles extend from the front surface of the head plate and the bottom ends of the bristles are adjacent to the rear surface of the head plate. After the bristles are inserted into the holes in the head plate, the bottom ends of the bristles are melted together by applying heat thereto, thereby forming a melt matte at the rear surface of the head plate. The melt matte is a thin layer of plastic that is formed by melting the bottom ends of the bristles so that the bottom ends of the bristles transition into a liquid, at which point the liquid of the bottom ends of the bristles combine together into a single layer of liquid plastic that at least partially covers the rear surface of the head plate. After the heat is no longer applied, the melted bottom ends of the bristles solidify/harden to form the melt matte/thin layer of plastic. In some embodiments, after formation of the melt matte, a tissue cleanser is injection molded onto the rear surface of the head plate, thereby trapping the melt matte between the tissue cleanser and the rear surface of the head plate. In other embodiments, other structures may be coupled to the rear surface of the head plate to trap the melt matte between the rear surface of the head plate and such structure without the structure necessarily being a tissue cleanser (the structure can just be a plastic material that is used to form a smooth rear surface of the head, or the like).

Of course, techniques other than AFT and AMR can be used for mounting the tooth cleaning elements 115 to the head 110, such as widely known and used stapling techniques or the like. In such embodiments, the head plate 130 may be omitted and the tooth cleaning elements 115 may be coupled directly to the head 110. Furthermore, in a further modified version of the AFT and AMR processes discussed above, the head plate 130 may be formed by positioning the tooth cleaning elements 115 within a mold, and then molding the head plate 130 around the tooth cleaning elements 115 via an injection molding process.

Referring again to FIGS. 1 and 2, in the exemplified embodiment the plurality of tooth cleaning elements 115 includes a plurality of separate tufts of bristles 114 and a plurality of elastomeric tooth cleaning elements 103. Although illustrated herein as having a specific arrangement and shape, the arrangement of the tufts of bristles 114 and elastomeric tooth cleaning elements 103 as well as the shapes thereof can be modified from that which is depicted in the figures. Thus, the collective tooth cleaning elements 115 can be any pattern or arrangement and each one of the tooth cleaning elements 115 can have any desired shape.

Referring now to FIG. 4, the head 110 may comprise one or more chambers 160 that forms a cavity where the body 156 of the release component 150 is positioned. The chamber 160 may comprise a floor 163 and a plurality of sidewalls 162 that extend upward from the floor 163. The sidewalls 162 may interest an upper surface 161.

Referring now to FIG. 7, in another embodiment, the release component 150 comprises a body 156 formed from a polymeric matrix and a release component embedded therein. The body 156 includes a lower surface 152 that is opposite an upper surface 151, whereby a side surface 152 extends between the lower surface 152 and the upper surface 151. The lower surface 152 of the body 156 of the release component 150 may be in direct contact with the lower surface 107 of the melt matte 106. The upper surface 151 of the release component 150 may face opposite of the lower surface 107 of the melt matte 106.

The head 110 may comprise a chamber 160 that forms a cavity where the body 156 of the release component 150 is positioned. The chamber 160 may comprise an upper surface 161 that is opposite the lower surface 107 of the melt matte 106. The upper surface 161 may be circumscribed by a plurality of sidewalls 163. The head 110 may further comprise one or more apertures 170 that extend from the rear surface 112 of the head 110 to the upper surface 161 of the chamber 160. The apertures 170 allow for at least a portion of the release component 150 to reach the rear surface 112 of the head 110 in the form of release islands 158 present on the rear surface 112 of the head 110. The upper surface 161 and the sidewalls 163 of the chamber 160 may be formed by a main body 144 of the head 110—as discussed further herein.

Referring to FIGS. 3-7 concurrently, the head 110 of the oral care implement 100 will be described in more detail. As noted above, the head 110 comprises the front surface 111, the rear surface 112 opposite the front surface 111, and the peripheral surface 113 extending between the front and rear surfaces 111, 112. The peripheral surface 113 forms a periphery of the head 110 and defines the outermost boundary of the head 110.

The head 110 of the oral care implement 100 comprises a main body 144 that is formed of a hard-plastic material, such as any of the materials noted above for forming the handle 120 (including polypropylene and the like). Furthermore, the head 110 comprises a release component 150 that is coupled to the main body 144. The release component 150 may comprise a polymeric matrix and a release agent. The release agent may be uniformly distributed throughout the polymeric matrix of the release component 150.

As discussed in greater detailed herein, the polymeric matrix of the present invention is a water-dissolvable composition that allows for a slow-release of the release agent from the release component 150 over time as the release component 150 is exposed to water (e.g., a user's saliva). The term "slow release" refers to a substantially continuous release of the release agent from the release component 150 over the course of at least three months based on exposure to water at least once a day—preferably twice a day—for a time period suitable for tooth brushing.

The release agent may be selected from any suitable compositions based on the desired effect over the slow release time period. For example, the release agent may be a colorant having a predetermined color (e.g., red, yellow, blue, orange, etc.), a flavoring agent, anti-bacterial or microbial agent, whitening agents (e.g., hydrogen peroxide), and the like. Non-limiting examples of release agent include zinc oxide, activated charcoal, L-arginin, and combinations thereof. In some embodiments, the release agent may be a blend of L-arginin and zinc oxide.

In a non-limiting example, the release component 150 may be a colorant. As the polymeric matrix is exposed to water during continual usage of the oral care implement—e.g., routine tooth brushing—the colorant will be depleted from the release component 150, which causes a corresponding color change in the release component 150. The change in color over time can provide a visual indication of the amount of usage of the oral care implement. With enough color change corresponding to the maximum recommended usage of the oral care implement, a user can be informed when it is an appropriate time to replace the oral care implement. In similar embodiments, the release agent can be a flavoring agent—whereby the release of the flavoring agent causes a corresponding loss of flavor levels in the release component 150. The loss of flavor indicates an appropriate time to replace the oral care implement. Additionally, the release agent can be a flavoring agent, whereby the release of the flavoring agent a change in flavor profile. The change in flavor profile can provide a complementary sensorial or polarizing flavor experience to the user.

In other embodiments, the oral care implement may comprise an anti-bacterial or anti-microbial agent (or a whitening agent) that does not provide a visual or taste indication of when to replace the oral care implement. Rather, in these embodiments, the release agent may be provided in an amount based on the release profile of the polymeric matrix, which is correlated to the typical lifespan of an oral care implement. In a non-limiting example, the release agent may be activated charcoal—i.e., an anti-microbial agent. For an oral care implement having a predetermined lifespan based on regular usage and comprising the release component 150, the anti-microbial agent may be present in the release component 150 in a pre-selected concentration that allows for continual release of the anti-microbial agent from the release component 150 over the entirety of that predetermined lifespan. Additionally, the concentration of the anti-microbial agent may be pre-selected such that once the predetermined lifespan of the oral care implement is completed, the release component 150 may be substantially depleted of the anti-microbial agent.

Generally, the release agent may be present in an amount ranging from about 0.1 wt. % to about 15.0 wt. % based on the total weight of the release component 150—including all amounts and sub-ranges there-between. Based on the desired release agent (i.e., colorant vs. anti-microbial agent), the specific concentration of the release agent within the release component 150 may vary. In a non-limiting example, zinc oxide may be the release agent and present in a concentration ranging from about 0.5 wt. % to about 4.0 wt. %—preferably about 2.0 wt. %—based on the total weight of the release component 150, including all amounts and sub-ranges there-between. In a non-limiting example, activated charcoal may be the release agent and present in a concentration ranging from about 0.1 wt. % to about 2.0 wt. %—preferably about 0.5 wt. % to about 1.0 wt. %—based on the total weight of the release component 150, including all amounts and sub-ranges there-between. In a non-limiting example, L-arginin may be the release agent and present in a concentration ranging from about 4 wt. % to about 15 wt. %—preferably about 5.0 wt. % to about 10 wt. %—based on the total weight of the release component 150, including all amounts and sub-ranges there-between.

The release component 150 may further comprise a non-releasable additive that is dispersed within the polymeric matrix. The non-releasable additive may be an organic or inorganic particle. In a preferred embodiment the non-releasable additive comprises an inorganic particle having either a uniform or varied particle size. In a non-limiting example, the inorganic particle may provide a textured feel to the release component 150.

The polymeric matrix of the present invention comprises a first polymer. The first polymer is a graft polymer. The graft polymer may comprise units that are formed from at least one of the following compounds I, II, III, and/or IV:

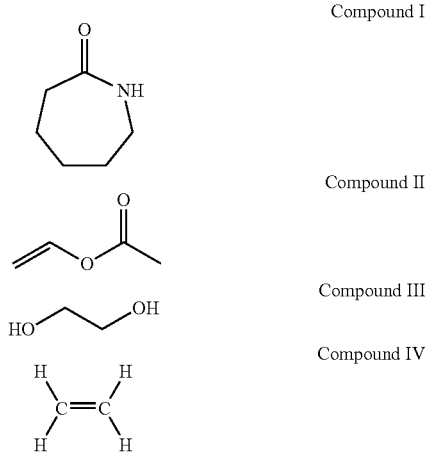

Compound I

Compound II

Compound III

Compound IV

Wherein Compound I is caprolactam, Compound II is vinyl acetate, Compound III is ethylene glycol, and Compound IV is ethylene. The term "graft polymer" is an art accepted term referring to segmented copolymers having a linear backbone of one composite and randomly distributed branches of another composite. Therefore, the graft polymer that is the first polymer may have branches formed from at least one of the Compounds I, II, III, and/or IV. In some embodiments, the first polymer may be polyvinyl caprolactam-polyvinylacetate-polyethylene glycol graft polymer. The first polymer may be a resilient and flexible elastomeric material, such as a thermoplastic elastomer. According to some embodiments, the polymeric matrix may be formed from about 100 wt. % of the first polymer.

According to some embodiments, the polymeric matrix may comprise a second polymer. The second polymer may be different from the first polymer. The second polymer may be polyvinylpyrrolidone. The first and second polymer may be present in the polymeric matrix in a weight ratio ranging from about 7:1 to about 11:1—preferably about 8:1 to about 10:1—including all ratios and subranges there-between. is a graft polymer. In a preferred embodiment, the first and second polymer may be present in the polymeric matrix in a weight ratio of about 9:1.

According to some embodiments, the polymeric matrix may comprise a fatty component. The fatty component may be a fatty acid. The fatty acid may have the following formula I:

Formula I

Wherein R may be a C14, C15, C16, C17, C18, C19, or C20 linear carbon chain. In a referred embodiment, R may be selected from a C16, C17, or C18 linear carbon chain. The R carbon chain may be saturated or contain unsaturated C=C bonds. The first polymer and the fatty component may be present in the polymeric matrix in a weight ratio ranging from about 7:1 to about 11:1—preferably about 8:1 to about 10:1—including all ratios and subranges there-between. is a graft polymer. In a preferred embodiment, the first polymer and the fatty component may be present in the polymeric matrix in a weight ratio of about 9:1.

The release component 150 of the present invention may be formed by injection molding a blend of the release agent and the first polymer. The benefit of using the first polymer to form the polymeric matrix is that the release component 150 may be formed at a processing temperature ranging from about 110° C. to about 200° C.—including all temperature and sub-ranges there-between. Although not explicitly recited, the phrase "including all temperature and sub-ranges there-between" is meant to encompass all integer values that exist between the lower limit temperature of 110° C. and the upper limit temperature of 200° C. For example, the temperature range from about 110° C. to about 200° C.—including all temperature and sub-ranges there-between—includes sub-ranges extending from about 130° C. to about 200° C. Additionally, the term "processing temperature" refers to a temperature at which a precursor composition—i.e., a blend of the first polymer and release agent, optionally with the second polymer and/or fatty component—is injection molded directly onto the head 110 of the oral care implement 100 to form the release component 150, whereby the resulting polymer matrix does not degrade and does not burn.

In some embodiments, the processing temperature of the polymeric matrix is greater than or equal to 130° C. In particular, the processing temperature may range from 130° C. to about 200° C.—including all temperatures and sub-ranges there-between. In some embodiments, the processing temperature of the polymeric matrix is greater than or equal to 135° C. In particular, the processing temperature may range from 135° C. to about 200° C.—including all temperatures and sub-ranges there-between. In some embodiments, the processing temperature of the polymeric matrix is greater than or equal to 140° C. In particular, the processing temperature may range from 140° C. to about 200° C.—including all temperatures and sub-ranges there-between. In some embodiments, the processing temperature of the polymeric matrix is greater than or equal to 145° C. In particular, the processing temperature may range from 145° C. to about 200° C.—including all temperatures and sub-ranges there-between. In some embodiments, the processing temperature may be greater than or equal to about 150° C. These processing temperatures may result in the formation of the release component 150 on the head 110 of the oral care implement 100.

The first polymer—alone or in combination with the second polymer and/or the fatty component—provides for a precursor composition that can be further blended with the release agent and processed at high temperatures in an injection molding process. The benefit is the formation of a water-dissolvable release component 150 that allows for a slow-release of the release agent from the release component 150 over time when the release component 150 is exposed to water (e.g., a user's saliva). Previously, water-dissolvable compositions were not able to be processed at such high temperatures without substantial degradation of the material and/or loss of slow-release performance. However, it has been discovered that by using the first polymer described herein, the resulting release component 150 can achieve both (1) the desired slow release water-dissolvable characteristics and (2) be processed at high temperatures that are suitable for injection molding, thereby facilitating production of the oral care implement but decreasing manufacturing time.

According to the present invention, not only can the release component 150 be formed using processing temperatures greater than or equal to 110° C. (preferably, greater than or equal to 120° C., 130° C., 140° C., and 150° C.) without degradation or the polymeric matrix, but it has been surprisingly discovered that the polymeric matrix further prevents certain release components from decomposing and/or prematurely being released during the manufacture of the release component 150.

The following a non-limiting example is provided to better explain this phenomenon—the release component may be an additive that is a whitening agent (e.g., hydrogen peroxide). Such additives may have a decomposition temperature that is less than processing temperature. Stated otherwise, the release agent and the first polymer (and second polymer, if present) may be processed at a temperature that is greater than the decomposition temperature of the release component. According to the present invention, the term "decomposition temperature" is a temperature at which a compound transforms from a first chemical composition into a second chemical composition that is chemically distinct from the first from the first chemical composition. For example, hydrogen peroxide may decompose at a temperature of about 150° C. into water ($H_2O$) and Oxygen ($O_2$). Therefore, previously, it was undesirable to process such release components at temperatures above their decomposition temperature due to the release components being modified into different chemically distinct compounds that resulted in the loss of the desired additive benefit (e.g., tooth whitening). However, it has been surprisingly discovered that the first polymer provides an unexpected protective benefit to such release components—even when the first polymer and the release component are processed at temperatures above the decomposition temperature of the release agent. Although the non-limiting example discussed herein is directed to hydrogen peroxide—which has a decomposition temperature of 150° C.—it should be understood that other release components may also benefit from the unexpected protective nature of the first polymer at other decomposition temperatures (i.e., the decomposition temperature of the release agent is not limited to 150° C.). Rather, the present invention is directed to the general relationship that release components may be processed at temperature exceeding their decomposition temperature without the release component being modified into a different chemically distinct compound and/or compounds.

In another non-limiting example, the release component may be a flavoring agent having a volatile nature. Such volatile nature is due to the high vapor pressure of such flavoring agents at relatively low temperatures (i.e., room temperature). When these flavoring agents are exposed to high processing temperatures (i.e., ≥110° C.), there is a substantial risk of fuming or vapor formation, thereby resulting in a premature release such flavor agents from the polymeric matrix. In a non-limiting example, the flavoring agent may be menthol—which has a vapor pressure of about 0.197 atm at 100° C. However, it has been surprisingly discovered that using the first polymer—alone or in combination with the second polymer and/or the fatty component—surprisingly eliminates the release of fumes and/or vapor even at high processing temperatures (i.e., ≥110° C.), thereby eliminating premature loss of volatile flavoring agents from the polymeric matrix during formation of the release component 150 at high processing temperatures. Therefore, the present invention further includes that the release component 150 may further comprise flavoring agents that exhibit a vapor pressure of at least 0.18 atm at 100° C.—preferably at least about 0.19 atm at about 100° C., even more preferably about 0.2 atm at about 100° C.—without substantial risk of fuming or vapor formation, thereby preventing the premature release such flavor agents from the polymeric matrix.

Referring now to FIG. 7, the release component 150 may be formed by injection molding a blend of the first polymer and release component (as well as the second polymer and/or the fatty component) into the cavity formed by the chamber 160. Specifically, before the melt-matte 106 and head plate 130 are attached to the head 110, the blend of the first polymer and release component (as well as the second polymer and/or the fatty component) are injection molded into the chamber 160 via the opening on the front surface 111 of the head 110. The release component 150 contacts the sidewalls 163 and upper surface 161 of the chamber 160, and at least a portion of the release component 150 passes through the apertures 170 to be exposed on the rear surface 112 of the head. Once cooled, the portion of the body 156 that remains within the chamber 160 and contacts the upper surface 161 acts as an anchor thereby holding the release islands 158 in place on the rear surface 112 of the head 110. Additionally, once the release component 150 is inserted into the chamber 160, the release component 150 may be in direct contact with at least one of the sidewall 163 and/or the upper surface 161 that is formed of polypropylene.

The release islands 158 may extend through the apertures 170 and beyond the main body 144 in a direction extending from the front surface 111 to the rear surface 112 of the head 110 such that a top portion of the release island 158 is taller than the main body 144 on the rear surface 112 of the head 110.

Additionally, the size of the apertures 170 may be modified to control the exposed surface area of the release component 150 on the rear surface 112 of the head 110. By controlling the exposed surface area of the release component 150 via controlling the size of the release islands 158, the amount of the release agent that can be released from the release component 150 within a given period can also be modified. For example, when the apertures 170 increase in size, the amount of release agent that can be delivered to a user's mouth may also be increased without changing the innate release characteristics of the first polymer. Conversely, when the apertures 170 decrease in size, the amount of release agent that can be delivered to a user's mouth may also be decrease without modifying the innate release characteristics of the first polymer.

According to such embodiments, the release component 150 may create a varied texture on the rear surface 112 of the head 110. In other embodiments, the top portion 151 of the release component 150 may be substantially flush with the rear surface 112 of the head 110.

Although not pictured, the oral care implement may further comprise elastomeric soft tissue cleansers that serve to clean the user's tongue and soft tissue surfaces and to protect the user's gums. The soft tissue cleansers may comprise protuberances that extend outward from the head 110. The elastomeric soft tissue cleanser may be positioned on the peripheral surface 113 of the head 110 and thus reduces the impact of the hard plastic of the base 144 against the user's gums during use of the toothbrush. The elastomeric soft tissue cleanser may also include raised features that protrude beyond the rear surface 112 of the head 110 and can also be used for cleaning/scraping a user's tongue. The elastomeric soft tissue cleanser may also be positioned on the rear surface 112 of the head 110 and surround the release component 150—i.e., not cover the release component 150. On the rear surface 112 of the head 110, the elastomeric soft tissue cleanser can be used to clean and scrub a user's tongue and other soft tissue surfaces. The elastomeric soft tissue cleanser on the rear surface 112 and/or the peripheral surface 113 results in a highly desirable aesthetic appearance for the oral care implement 100.

The protuberances present on the elastomeric soft tissue cleanser may be in the form of a nub. As used herein a "nub" generally refers to a column-like protrusion (without limitation to the cross-sectional shape of the protrusion) which is upstanding from a base surface. In a general sense, the protuberances in the preferred construction have a height that is greater than the width at the base of the protuberance (as measured in the longest direction). Nevertheless, protuberances or nubs could include projections wherein the widths and heights are roughly the same or wherein the heights are somewhat smaller than the base widths. Moreover, in some circumstances (e.g., where the protuberances taper to a tip or include a base portion that narrows to a smaller projection), the base width can be substantially larger than the height. Furthermore, in the exemplified embodiment the plurality of protuberances may have varying heights such that some of the protuberances are taller than other of the protuberances. The elastomeric soft tissue cleanser may be a flexible material, such as a thermoplastic elastomer.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. An oral care implement comprising:
 a handle; and
 a head having a main body that is coupled to the handle, the main body having an outer surface, the head comprising:
  a plurality of tooth cleaning elements;
  at least one chamber formed into the outer surface of the main body, the chamber comprising a floor, at least one side wall, and an upper surface, each of the floor, the at least one side wall, and the upper surface formed by the main body;
  a release component coupled to the main body and located inside of the at least one chamber such that the release component directly contacts the floor of the chamber, the release component comprising:
   a water-dissolvable matrix comprising a first polymer having a processing temperature greater than or equal to 130° C.; and
   a plurality of upper surfaces protruding above the outer surface of the main body.

2. The oral care implement of claim 1, wherein the head further comprises
 a front surface;
 a rear surface opposite the front surface;
 a peripheral surface extending between the rear surface and the front surface; and
 the plurality of tooth cleaning elements extending from the front surface.

3. The oral care implement according to claim 1, wherein the first polymer is a graft copolymer comprising units formed from caprolactam, vinyl acetate, and ethylene glycol.

4. The oral care implement according to claim 1, wherein the water-dissolvable matrix further comprises a fatty acid, wherein the first polymer and the fatty acid are present in a weight ratio ranging from about 8:1 to about 10:1, and wherein the fatty acid includes a C16 to C18 carbon chain.

5. The oral care implement according to claim 1, wherein the water-dissolvable matrix further comprises a second polymer that is different from the first polymer, wherein the first polymer and the second polymer are present in a weight ratio ranging from about 8:1 to about 10:1.

6. The oral care implement according to claim 5, wherein the second polymer comprises polyvinylpyrrolidone.

7. The oral care implement according to claim 1, wherein the release component further comprises a release agent comprises one or more compounds selected from the group of zinc oxide, activated charcoal, L-arginin, flavor agents, and colorants.

8. The oral care implement according to claim 1, wherein the release agent is present in an amount ranging from about 0.1 wt. % to about 15 wt. % based on the total weight of the release component.

9. The oral care implement according to claim 1, wherein the head comprises a rear surface, the rear surface comprising the release component.

10. The oral care implement according to claim 1, wherein the main body is formed from polypropylene.

11. The oral care implement of claim 1 wherein each one of the plurality of upper surfaces extends through an aperture formed between the outer surface of the main body and the upper surface of the chamber.

12. The oral care implement of claim 1 wherein the head comprises a head plate, the plurality of tooth cleaning elements extending through the head plate and forming a melt matte, a lower surface of the melt matte in contact with the release component.

13. An oral care implement comprising:
 a handle; and
 a head having a main body coupled to the handle, the main body having an outer surface, the head comprising:
  at least one chamber formed into the outer surface of the main body, the chamber comprising a floor, at least one side wall, and an upper surface, each of the floor, the at least one side wall, and the upper surface formed by the main body;

a release component comprising a water-dissolvable matrix comprising a graft polymer having units formed from caprolactam, vinyl acetate, and ethylene glycol, the release component located inside of the at least one chamber such that the release component directly contacts the floor of the chamber, a plurality of upper surfaces protruding above the outer surface of the main body; and a plurality of tooth cleaning elements.

14. The oral care implement of claim 13, wherein the head further comprises
a front surface;
a rear surface opposite the front surface;
a peripheral surface extending between the rear surface and the front surface; and
the plurality of tooth cleaning elements extending from the front surface.

15. The oral care implement according to claim 13, wherein the water-dissolvable matrix further comprises a fatty acid, wherein the first polymer and the fatty acid are present in a weight ratio ranging from about 8:1 to about 10:1, and wherein the fatty acid includes a C16 to C18 carbon chain.

16. The oral care implement according to claim 13, wherein the water-dissolvable matrix further comprises a second polymer that is different from the first polymer, wherein the first polymer and the second polymer are present in a weight ratio ranging from about 8:1 to about 10:1.

17. The oral care implement according to claim 16, wherein the second polymer comprises polyvinylpyrrolidone.

18. The oral care implement according to claim 13, wherein the main body is formed from polypropylene.

19. An oral care implement comprising:
a handle; and
a head having a main body that is coupled to the handle, the head comprising:
a front surface and a rear surface;
a cavity located inside of the main body, the cavity comprising a floor, a plurality of sidewalls, and an upper surface formed by the main body;
at least one aperture formed into the rear surface of the head, the aperture extending from the rear surface of the head to the upper surface of the cavity;
a release component coupled to the main body and positioned in the cavity, wherein a first portion of the release component is exposed on the rear surface of the head through the at least one aperture and a second portion is concealed inside of the cavity by the rear surface of the head, the first portion of the release component protruding beyond the rear surface of the head; and
a plurality of tooth cleaning elements;
wherein the release component comprises a water-dissolvable matrix comprising a first polymer having a processing temperature greater than or equal to 130° C.

20. The oral care implement of claim 19 comprising a plurality of apertures extending between the rear surface of the head and the upper surface of the cavity.

* * * * *